United States Patent [19]

Smith

[11] Patent Number: 5,753,452

[45] Date of Patent: May 19, 1998

[54] REAGENT TEST STRIP FOR BLOOD GLUCOSE DETERMINATION

[75] Inventor: John L. Smith, Los Altos, Calif.

[73] Assignee: Lifescan, Inc., Milpitas, Calif.

[21] Appl. No.: 627,630

[22] Filed: Apr. 4, 1996

[51] Int. Cl.$^6$ .................. C12Q 1/54; C12Q 1/00; G01N 33/53; G01N 21/00
[52] U.S. Cl. .................. 435/14; 435/4; 435/287.1; 435/970; 435/808; 422/50; 422/55; 422/68.1
[58] Field of Search .................. 435/14, 4, 287, 435/970, 808, 287.1; 422/50, 55, 68.1

[56] References Cited

U.S. PATENT DOCUMENTS

| | | | |
|---|---|---|---|
| 4,935,346 | 6/1990 | Phillips et al. | 435/14 |
| 5,304,468 | 4/1994 | Phillips et al. | 435/14 |
| 5,306,623 | 4/1994 | Kiser et al. | 435/14 |
| 5,453,360 | 9/1995 | Yu | 435/28 |

OTHER PUBLICATIONS

Capaldi, Dante J. and Taylor, Keith E. Analytical Biochemistry 129, 329–336 (1983) "A new Peroxidase Color Reaction: Oxidative Coupling of 3–Methyl–2–Benzothiazolinone Hydrazone (MBTH) with its Formaldehyde Azine. Application to Glucose and Choline Oxidases" month not available.

*Primary Examiner*—Louise Leary
*Attorney, Agent, or Firm*—James Riesenfeld

[57] ABSTRACT

A reagent test strip is adapted for use in a blood glucose meter. A sample of whole blood is applied to one surface of a matrix on the strip and the meter measures the reflectance of the opposite surface of the matrix at about 635 nm and 700 nm and calculates from the reflectances the concentration of glucose in the sample. The portion of the applied sample that penetrates the matrix and is visible from the testing surface does not absorb to any appreciable extent at 700 nm. Nevertheless, the glucose-containing sample interacts with the components of the reagent-containing matrix to cause a change in reflectance at 700 nm that simulates the effect of the blood color. As a result, the strip can be used in meters that measure glucose concentration in whole blood samples in the presence of optically visible hemoglobin.

13 Claims, 1 Drawing Sheet

REAGENT TEST STRIP FOR BLOOD GLUCOSE DETERMINATION

BACKGROUND OF THE INVENTION

1. Field of the Invention

This invention relates to a dry test strip for measuring the concentration of an analyte in a biological fluid; more particularly, a test strip that colorimetrically measures the concentration of glucose in whole blood.

2. Description of the Related Art

Many visual test devices have been developed for measuring the concentration of certain analytes in biological fluids. These devices have, for example, measured glucose, cholesterol, proteins, ketones, phenylalanine, or enzymes in blood, urine, or saliva.

Dry phase reagent strips incorporating enzyme-based compositions are used extensively in hospitals, clinical laboratories, physician's offices, and homes to test samples of biological fluids for glucose concentration. In fact, reagent strips have become an everyday necessity for many of the nation's several million diabetics. Since diabetes can cause dangerous anomalies in blood chemistry, it can contribute to vision loss, kidney failure, and other serious medical consequences. To minimize the risk of these consequences, current teaching counsels persons with diabetes to measure their blood glucose level from two to seven times a day, depending on the nature and severity of their individual cases. Based on the observed pattern in the measured glucose levels, the patient and physician together make adjustments in diet, exercise and insulin intake to better manage the disease. Clearly, this information should be available to the patient immediately, through the use of a simple-to-use meter and strip system that is rapid, inexpensive, and accurate.

Reagent strips are known that contain an indicator which turns a different shade of color, depending on the concentration of glucose in a biological fluid that has been applied to the strip. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide.

U.S. Pat. No. 4,935,346, issued Jun. 19, 1990 to R. Phillips et al., discloses a meter, strip, and method for determining the glucose concentration in a sample of whole blood (see also U.S. Pat. No. 5,304,468). The method involves simply applying a sample of whole blood to a first ("sample") surface of an inert porous matrix that is impregnated with a reagent. The sample migrates toward the opposite, "testing" surface, as the glucose interacts with the reagent to produce a light-absorbing reaction product. A reading of reflectance from the testing surface indicates the glucose concentration. Reflectance measurements are made at two separate wavelengths in order to eliminate interferences. A timing circuit is triggered by an initial decrease in reflectance caused by wetting of the testing surface by the sample having passed through the matrix.

U.S. Pat No. 5,306,623, issued Apr. 26, 1994 to Kiser et al., discloses a visual blood glucose test strip that involves applying a glucose-containing whole blood sample to one side of the strip and taking the glucose reading on the opposite side, after red blood cells have been separated out and the sample has reacted with a reagent in the strip. An anisotropic polysulfone membrane was found especially useful as a single layer matrix for the strip.

U.S. Pat No. 5,453,360, issued Sep. 26, 1995 to Y. S. Yu, discloses a dye couple useful in dry reagent strips for detecting analytes, such as glucose, in biological fluids. The dye couple comprises 3-methyl-2-benzothiazolinone hydrazone and 8-anilino-1-naphthalenesulfonate and is used as an indicator in a reaction cascade producing a strong oxidizing agent, such as hydrogen peroxide. An advantage of the couple is that it is soluble in aqueous solution, but becomes insoluble upon oxidative coupling, thereby minimizing fading and providing a stable endpoint.

A meter that has come into widespread use for self-monitoring of blood glucose is the One Touch® II meter, which uses a strip that is described in U.S. Pat. Nos. 4,935,346 and 5,304,468, discussed above. The meter and strip permit a user to measure glucose concentration in a whole blood sample quickly, easily, and accurately. The sample is applied to one surface of the strip and the measurement made on the opposite surface. A portion of the whole blood sample penetrates from the sample surface to the testing surface, and the blood color can be observed from the testing surface.

SUMMARY OF THE INVENTION

The present invention provides a reagent test strip for use in an apparatus for determining a concentration of glucose in a sample of whole blood. The apparatus comprises optical means for detecting intensity of light at wavelengths of about 635 nm and about 700 nm reflected from at least a portion of a matrix disposed near one end of the strip, which matrix comprises (a) a sample receiving surface for receiving the whole blood sample and passing a portion of it toward a testing surface opposite thereto, (b) a structure that selectively retards the passage of red blood cells through the matrix and minimizes the lysing of the cells in the matrix, whereby any portion of the sample that is visible from the testing surface does not absorb light to any appreciable extent at about 700 nm, and (c) a reagent for indicating the glucose concentration by creating at the testing surface a change in reflectance at about 700 nm that is substantially equivalent to that produced by the absorbance of hemoglobin in blood and a change in reflectance at about 635 nm that is indicative of the glucose concentration.

In the present specification and the appended claims, reference to the fact that "sample that is visible from the testing surface does not absorb light to any appreciable extent at about 700 nm" means 700 nm absorbance by the sample, as seen through the testing surface, is less than about 20% of the 700 nm absorbance caused by the reaction of the sample with the reagent.

Another embodiment of the present invention also provides a reagent test strip for use in an apparatus for determining a concentration of glucose in a sample of whole blood. The apparatus comprises optical means for detecting intensity of light at wavelengths of about 635 nm and about 700 nm reflected from at least a portion of a matrix disposed near one end of the strip, which matrix comprises (a) a sample receiving surface for receiving the whole blood sample and passing a portion of it toward a testing surface opposite thereto, the testing surface having a reflectance at about 700 nm that, when the testing surface becomes wet, undergoes a change that is substantially equivalent to that produced by the absorbance of hemoglobin in blood, (b) a structure that selectively retards the passage of red blood cells through the matrix and minimizes the lysing of the cells in the matrix, whereby any portion of the sample that is visible from the testing surface does not absorb light to any appreciable extent at about 700 nm, and (c) a reagent for indicating the glucose concentration by creating at the testing surface a change in reflectance at about 635 nm.

The invention provides a reagent test strip that is suitable for use in a One Touch® whole blood glucose meter. Since the structure of the strip selectively retards the passage of red blood cells through the matrix and minimizes their lysing, the glucose determination is relatively independent of the hematocrit of the whole blood sample.

DETAILED DESCRIPTION OF THE INVENTION

Figure 1:
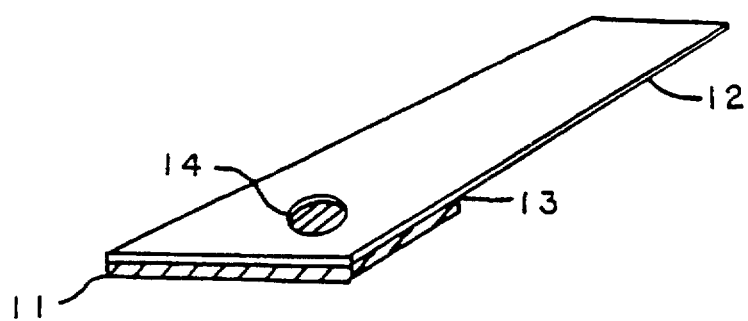
FIG. 1 is a perspective view of an embodiment of a test strip of this invention.

This invention provides a rapid and simple method, employing a reliable and easy to operate apparatus, for the determination of glucose in whole blood. The method involves applying to one surface (the "sample" surface) of an inert porous matrix a small sample of whole blood, sufficient to saturate the matrix. The matrix is typically present in a reflectance-measuring apparatus when blood is applied. At least a portion of the liquid sample penetrates the matrix, resulting in an initial change in reflectance at the opposite ("testing") surface. The glucose in the sample reacts with one or more reagents bound to the matrix to form a product that changes the reflectance of the matrix. A reading is then taken at one or more times after the initial change in reflectance to relate the further change in reflectance at the testing surface or in the matrix to the concentration of glucose in the sample.

FIG. 1 shows one embodiment of the present invention. A thin hydrophilic matrix reagent pad 11 is positioned at one end of a plastic holder 12 by means of an adhesive 13, which directly and firmly attaches the reagent pad to the holder. The holder, which is optional, provides physical form and rigidity to the strip. A hole 14 is present in the plastic holder 12 in the area to which reagent pad 11 is attached, so that sample can be applied through hole 14 to the sample side of the reagent pad and light reflected from the other, testing side.

A whole blood sample to be tested is applied to pad 11. Generally, the reagent pad surface area is about 10 mm$^2$ to 100 mm$^2$, especially 10 mm$^2$ to 50 mm$^2$, which normally provides a volume that 5–10 µL of sample will more than saturate.

Additional details regarding the structure of the strip appear in the above-referenced U.S. Pats. Nos. 4,935,346, ('346) and 5,304,468 ('468), incorporated herein by reference.

The analysis method of this invention relies on a change in absorbance, as measured by diffuse reflectance, which is dependent upon the glucose concentration present in a sample being tested. This change may be determined by measuring the reflectance change over one or more time intervals.

In operation, the test strip is first mounted in an instrument for reading light absorbance; e.g., color intensity, by reflectance, prior to application of the sample. Then, a glucose-containing blood sample—obtained by a finger stick, for example—is applied to the matrix of the test strip. Preferably, the amount exceeds that needed to saturate the matrix in the area where reflectance will be measured (i.e., about 5–10 µL). After the sample is applied, timing of the measurement is initiated automatically when fluid penetrates the matrix, and the apparatus detects the resulting change in reflectance of the testing surface. The change in reflectance over a predetermined time, as a result of formation of reaction product, is then related to the glucose concentration in the sample. Reflectance refers in this specification and in the appended claims both to the visible wavelength range and to infrared and ultraviolet radiation.

A suitable instrument, such as a diffuse reflectance photometer with appropriate software, can be made to automatically read reflectance at one or more time intervals, calculate the reflectance change, and, using calibration factors, output the glucose concentration in the blood sample. Details of such an instrument, including the methodology used by the instrument to convert reflectance measurements into blood glucose concentrations, are provided in '346 and '468. In particular, commercially available One Touch® meters are suitable for use in combination with the reagent strip of the present invention to measure glucose concentrations in whole blood samples. These meters read reflectance of the strip testing surface at about 635 nm and about 700 nm.

The matrix of the present invention is preferably a membrane that effectively separates the red blood cells and hemoglobin from a whole blood sample to leave the glucose-containing plasma. The separation takes place as the sample moves through the membrane from the sample surface to the testing surface. A membrane to accomplish that separation may have pores that trap the red blood cells, generally pore sizes in the range from about 0.1 µm to about 5 µm. Preferably, the membrane is anisotropic, with a range of pore sizes; more preferably, a broad range of pore sizes. When the matrix comprises an anisotropic membrane, the sample side is preferably the large-pore side. For example, a gradient of pore sizes from about 0.1 µm to about 150 µm may extend through the membrane. On the large-pore side, pore size is preferably in the range from about 30 µm to about 40 µm. On the side of the membrane where the pores are smallest (i.e., the testing surface), the void volume is relatively small, and the material of the membrane is generally quite dense, within a layer that can typically constitute up to 20% of the membrane's thickness. Within this layer, pore size is preferably in the range from about 0.1 to about 0.8 µm, with a nominal pore size preferably about 0.3 µm.

When the whole blood sample is applied to the sample side, the sample encounters increasingly smaller pores as it penetrates the membrane. Eventually, solids such as red blood cells reach a position in the membrane, generally near the sample surface, where they can penetrate no further. The membrane not only traps red blood cells near the sample surface, but also minimizes lysing of the cells, so that any portion of the sample that is visible from the testing surface does not absorb light to any appreciable extent at about 700 nm. The balance of the sample, still containing the dissolved glucose, penetrates through to the testing side. As it passes through the membrane, glucose in the sample reacts with the reagent, causing a light-absorbing dye to be formed near the testing side, thereby substantially affecting reflectance from the testing surface. The anisotropic nature of the membrane and/or use of a separating component (discussed below)

permits relatively rapid flow rates through the membrane, even while separation of the solids is taking place.

The matrix is a hydrophilic porous membrane to which reagents may be covalently or non-covalently bound. The matrix allows for the flow of an aqueous medium through it. It also allows for binding of protein compositions to the matrix without significantly adversely affecting the biological activity of the protein, e.g. enzymatic activity of an enzyme. To the extent that proteins are to be covalently bound, the matrix will have active sites for covalent bonding or may be activated by means known to the art. The composition of the matrix is reflective, and it has sufficient thickness to permit the formation of a light absorbing dye in the void volume or on the surface to substantially affect the reflectance from the matrix. The matrix may be of a uniform composition or a coating on a substrate providing the necessary structure and physical properties, such as hydrophilicity.

Polysulfones and polyamides (nylons) are examples of suitable matrix materials. Other polymers having comparable properties may also be used. The polymers may be modified to introduce other functional groups which provide for charged structures, so that the surfaces of the matrix may be neutral, positive, or negative.

A preferred method of preparing the porous material that forms the matrix is to cast the polymer without a supporting core. Such a matrix is, for example, the anisotropic polysulfone membrane available from Memtec, Inc., Timonium, Md. The terms "matrix" and "membrane" are used interchangeably herein. Each term is understood to not be limited to a single layer and can include, for example, an absorbent layer. A matrix of less than about 500 μm thickness is usually employed, with about 115 to 155 μm being preferred. A thickness of about 130 to 140 μm is most preferred, particularly when the matrix is nylon or anisotropic polysulfone. The matrix generally does not deform on wetting, thus retaining its original conformation and size, and has sufficient wet strength to allow for routine manufacture.

The membrane has impregnated into its pores a testing reagent that is capable of reacting with glucose to produce a light-absorbing reaction product. The membrane may be treated with reagent by dipping it into a mixture of the components, thereby saturating the membrane. Excess reagent may be removed by mechanical means such as, for example, an air knife, doctor blade, or glass rod. The membrane is then dried. Reagent tends to concentrate near the small-pore (testing) side of the membrane. Other methods that are suitable for applying reagent to the membrane will occur readily to a person having ordinary skill in the art.

The testing reagent comprises a component for converting glucose to hydrogen peroxide and a component for detecting hydrogen peroxide. The reagent may optionally further comprise a separating component which causes solids, such as red blood cells, to become entrapped in the matrix, effectively removing the solids from the whole blood. Additional components may also be included as described below.

Preferred components for converting glucose to hydrogen peroxide include glucose oxidase, an enzyme that is usually obtained from Aspergillus niger or Penicillium. Glucose oxidase reacts with glucose and oxygen to produce gluconolactone and hydrogen peroxide. Optimum glucose oxidase concentration depends on the composition of the indicator system; however, glucose oxidase in the range from about 500–10,000 U./mL is generally suitable, more preferably from about 700–2000 U./mL. Generally, higher concentrations of glucose oxidase cause the reaction to proceed more rapidly and lower concentrations, less rapidly. Optimum concentration can be determined by routine experimentation.

The hydrogen peroxide so produced reacts with the component for detecting hydrogen peroxide, which comprises a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red hemin obtained from plants. Peroxidases obtained from animals, for example from the thyroid glands of animals, are also suitable. Horseradish peroxidase (HRPO) is especially preferred as a constituent of the component for detecting hydrogen peroxide. The hydrogen peroxide, preferably catalyzed by a peroxidase, reacts either directly or indirectly to form an indicator dye that reduces 635 nm reflectance at the testing surface. Testing surface reflectance is measured at two wavelengths —about 635 nm and about 700 nm.

Reflectance measurements are made in a timed sequence. The sequence is initiated by the reflectance reduction at 635 nm that results from the arrival of a portion of the sample at the testing surface. We denote this initiation of timing as "reflectance switching". The reflectance at 700 nm is measured 15 seconds later. By that time, the blood will have saturated the reagent pad, and the interaction of the glucose-containing blood sample with the reagent-containing membrane will have caused a reduction in reflectance at 700 nm that is substantially equivalent to the reduction produced by blood color being visible at the testing surface. Thus, although any sample that is visible from the testing surface does not absorb light to any appreciable extent at 700 nm, the meter detects the reduction in 700 nm reflection that it associates with absorption by the blood color, and that causes it to then make reflectance measurements at about 635 nm. The glucose concentration in the sample is calculated from the 635 nm reflectance, using the 700 nm reflectance to calculate a correction factor. Note that since blood absorbs at 635 nm, so too should the blood-simulating 700 nm absorber. Ideally, the blood-simulating material should have the same ratio of absorbance at 700 nm to absorbance at 635 nm as does whole blood, but for brevity we refer to the blood-simulating material's absorbance at 700 nm only. Details of the calculation, including the correction for the "blood" reflectance at 700 nm, appear in the aforementioned '346.

The reduced testing-surface reflectance at 700 nm that simulates the blood color can be effected in four alternative ways. First, the membrane may contain a component that absorbs 700 nm radiation and the testing surface may be substantially opaque until it becomes more transparent to 700 nm light when wet. The component that absorbs at 700 nm may be a nonwoven, for example, that is not visible from the dry testing surface. The component could also be a support onto which the membrane is cast, a coating on the sample surface of the membrane, or the like.

Second, the membrane may include a water soluble dye that has light absorbance at 700 nm that is substantially increased when the dye goes into solution. For example, the dye could initially be in the form of finely divided water-soluble crystals, applied to the membrane as dispersed solids that appear white and provide no substantial absorbance at 700 nm. The aqueous sample dissolves the dye, at which point it becomes colored and absorbs at 700 nm. An example of such a dye is copper phthalocyanine.

Third, the interaction between glucose and the reagent in the membrane can result in a chromophore that absorbs light at both 635 nm and 700 nm, thereby indicating glucose concentration and, at the same time, simulating the presence of blood.

Finally, the blood-reagent interaction can yield two chromophores, one of which absorbs at 635 nm and the other of which absorbs at 700 nm. Further, since only enough 700 nm reflectance reduction is needed to simulate the presence of blood color, preferably only a small amount of the chromophore that absorbs at 700 nm is present.

In the first two cases, in which 700 nm absorbance (i.e., reduced reflectance) results from another membrane component, the 700 nm absorbance does not require a chromophore. In the third and fourth cases, the reduction in 700 nm reflectance is effected by a chromophore. In each case, however, the reduction in 700 nm reflectance observed from the testing surface 15 seconds after reflectance switching must simulate the blood color, as is described in detail in '346.

The magnitude of the reduction in reflectance at 635 nm, adjusted as disclosed in '346, at a suitable time after initiation of the timing sequence, is a measure of the glucose concentration in the whole blood sample. Dye couples that are suitable as indicators include 4-aminoantipyrene (AAP) and chromotropic add; AAP and 8-anilino-1-naphthalenesulfonate (ANS); AAP and N-ethyl-N-(2 hydroxy-3-sulfopropyl)-m-toluidine (TOOS); 3-methyl-2-benzothiazolinone hydrazone hydrochloride (MBTH) and ANS; MBTH combined with 3-dimethylaminobenzoic add (DMAB); and MBTH combined with its formaldehyde azine.

Although the anisotropic membrane that is the preferred matrix filters out red blood cells and holds them away from the testing side, optionally the testing reagent may also contain a separating component, (see, for example, the aforementioned U.S. Pat. No. 5,306,623, to Kiser et al.) The separating component should be capable of producing a relatively clear colorless fluid from fluid containing red blood cells, e.g., whole blood, by sequestering red blood cells in the matrix and, preferably, also sequestering any small amounts of free hemoglobin. Separating components for use in the instant invention include but are not limited to polyethylene glycol, poly (methylvinyl ether/maleic) anhydride, polypropylene glycol, polystyrene sulfonic acid, polyacrylic acid, polyvinyl alcohol, and polyvinyl sulfonic acid at a pH of about 4.0–8.0. Such separating components are present in the matrix in amounts that will vary depending upon their charge and molecular weight, the other components imbedded in the matrix, the matrix pH and pore size, and the residual moisture of the matrix after drying. Such parameters are readily determinable by one skilled in the art For example, when polypropylene glycol is employed as the separating component (e.g., PPG-410 from BASF, Wyandotte, Mich.), it is preferably present at about 2–30% weight to volume (w/v), and more preferably 8–10% w/v. Other separating components can also be employed in a concentration of about 2–30% w/v. The polymeric separating components may be impregnated or imbedded in the matrix or cast in the membrane during manufacture.

Some water soluble salts can also effect blood separation. Among salts suitable for separating blood components are citrates, formates, and sulfates, as well as certain acids, such as amino acids, citric acid, phytic acid, and malic acid. (See, e.g., U.S. Pat No. 3,552,928, issued Jan. 5,1971, to M. C. Fetter.)

Separating components are preferably included in the testing reagent, because they increase the effectiveness of the membrane in ensuring that no appreciable amount of red blood gets through. They thus ensure that sample that is visible from the testing surface does not absorb light to any appreciable extent at 700 nm.

Other components may be imbedded into the matrix to enhance the coloration and readability of the reagent strips and to preserve the uniformity and integrity of the matrix. For example, the testing reagent may include salts and/or buffers to aid in the separation of the dye in the matrix. Such buffers may contain for example, citrate, present in solution at from about 0.01M to about 1.0M, and preferably at about 0.1M. Other buffers may also be employed.

Compounds that make the matrix hydrophilic or compounds that can act as stabilizers, such as hydrolyzed proteins, may also be employed. Such compounds include but are not limited to for example bovine serum albumin, polypeptides and the low molecular weight protein available as Crotein SPA (CRODA, Inc. New York, N. Y.). Such compounds are used at concentrations of for example about 1 mg/mL to about 100 mg/mL. In the case of Crotein, about 30 mg/mL is preferred.

Other stabilizers and preservatives may also be included in the coating for the matrix. For example ethylene diamine tetraacetic acid (EDTA), diethylene triamine pentaacetic acid (DTPA) and related compounds may be employed, for example, at concentrations of about 0.01 mg/mL to about 10 mg/mL.

Variations of the detail presented herein may be made without departing from the scope and spirit of the present invention.

I claim:

1. A reagent test strip having a matrix near one end for use in an apparatus for determining a concentration of glucose in a sample of whole blood, the apparatus comprising optical means for detecting intensity of light at wavelengths of about 635 nm and about 700 nm reflected from at least a portion of the matrix, which matrix comprises a) a sample receiving surface for receiving the whole blood sample and passing a portion of the sample toward a testing surface opposite thereto, the testing surface having a reflectance at about 700 nm that, when the testing surface becomes wet, undergoes a change that is substantially equivalent to that produced by the absorbance of hemoglobin in blood b) a structure that selectively retards the passage of red blood cells through the matrix and minimizes the lysing of the cells in the matrix, whereby any portion of the sample that is visible from the testing surface does not absorb light to any appreciable extent at about 700 nm, and c) a reagent for indicating the glucose concentration by creating at the testing surface a change in reflectance at about 635 nm.

2. The strip of claim 1 in which the matrix comprises a membrane that has pores that trap the red blood cells of the whole blood sample.

3. The strip of claim 1 in which the matrix comprises an anisotropic membrane.

4. The strip of claim 3 in which the membrane has pores that are larger near the sample receiving surface and smaller near the testing surface.

5. The strip of claim 1 in which the matrix comprises a polyamide membrane.

6. The strip of claim 1 in which the matrix has an interior region that absorbs 700 nm light and that is visible from the testing surface only when the surface is wet.

7. The strip of claim 6 in which the matrix interior region comprises a nonwoven material having substantial absorbance at 700 nm.

8. The strip of claim 1 in which the matrix further comprises a water-soluble dye that has light absorption at 700 nm that is substantially increased when the dye goes into solution.

9. The strip of claim 8 in which the dye comprises copper phthalocyanine.

10. The strip of claim 1 in which the reagent comprises a dye precursor that forms a chromophore indicative of the glucose concentration, the chromophore absorbing light at 635 nm.

11. The strip of claim 10 in which the reagent dye precursor is selected from the group consisting of 3-methyl-2-benzothlazolinone hydrazone hydrochloride (MBTH) with 3-dimethylaminobenzoic acid (DMAB); MBTH with 8-anilino-1-naphthalenesulfonate (ANS); MBTH with its formaldehyde azine and combinations thereof.

12. The strip of claim 11 in which the reagent dye precursor comprises MBTH and ANS.

13. The strip of claim 11 in which the reagent dye precursor comprises MBTH combined with DMAB.

* * * * *